(12) United States Patent
Junger

(10) Patent No.: US 7,470,249 B2
(45) Date of Patent: Dec. 30, 2008

(54) ASPIRATION AND FLUSHING NEEDLE

(75) Inventor: Michael Carl Junger, Queensland (AU)

(73) Assignees: William A. Cook Australia Pty. Ltd., Queensland (AU); Cook Incorporated, Bloomington, IN (US)

( * ) Notice: Subject to any disclaimer, the term of this patent is extended or adjusted under 35 U.S.C. 154(b) by 284 days.

(21) Appl. No.: 10/816,288

(22) Filed: Apr. 1, 2004

(65) Prior Publication Data

US 2004/0225180 A1    Nov. 11, 2004

Related U.S. Application Data

(60) Provisional application No. 60/459,311, filed on Apr. 1, 2003.

(51) Int. Cl.
*A61B 17/20* (2006.01)
(52) U.S. Cl. .............. 604/19; 604/22; 604/264; 604/43
(58) Field of Classification Search .......... 604/43, 604/264, 19, 22, 40, 158, 164.01, 164.09, 604/72
See application file for complete search history.

(56) References Cited

U.S. PATENT DOCUMENTS

| 3,561,596 | A | * | 2/1971 | Knox | 206/229 |
| 4,314,560 | A | * | 2/1982 | Helfgott et al. | 606/171 |
| 4,634,420 | A | * | 1/1987 | Spinosa et al. | 604/22 |
| 5,160,319 | A | * | 11/1992 | Emery et al. | 604/27 |
| 5,533,986 | A | * | 7/1996 | Mottola et al. | 604/264 |
| 6,018,676 | A | * | 1/2000 | Davis et al. | 600/431 |
| 6,273,877 | B1 | * | 8/2001 | West et al. | 604/264 |
| 6,979,339 | B2 | * | 12/2005 | Bishop et al. | 606/167 |

* cited by examiner

*Primary Examiner*—Nicholas D Lucchesi
*Assistant Examiner*—Laura A Bouchelle
(74) *Attorney, Agent, or Firm*—James B. Hunt

(57) ABSTRACT

An aspiration and flushing needle assembly having separable flushing and aspiration assemblies. The flushing assembly (2) has a flushing needle (27) extending from a handle (25) and a flushing fluid line (35) which can be connected to a source of flushing liquid. The aspiration assembly (1) has an aspiration needle (5) with a connector (9) which connects into the rear of the handle and an aspiration line (13) which can be connected to an aspiration arrangement. The flushing and aspiration needle assemblies are joined for use with the aspiration needle extending coaxially within the flushing needle to the distal end (29) of the flushing needle.

10 Claims, 4 Drawing Sheets

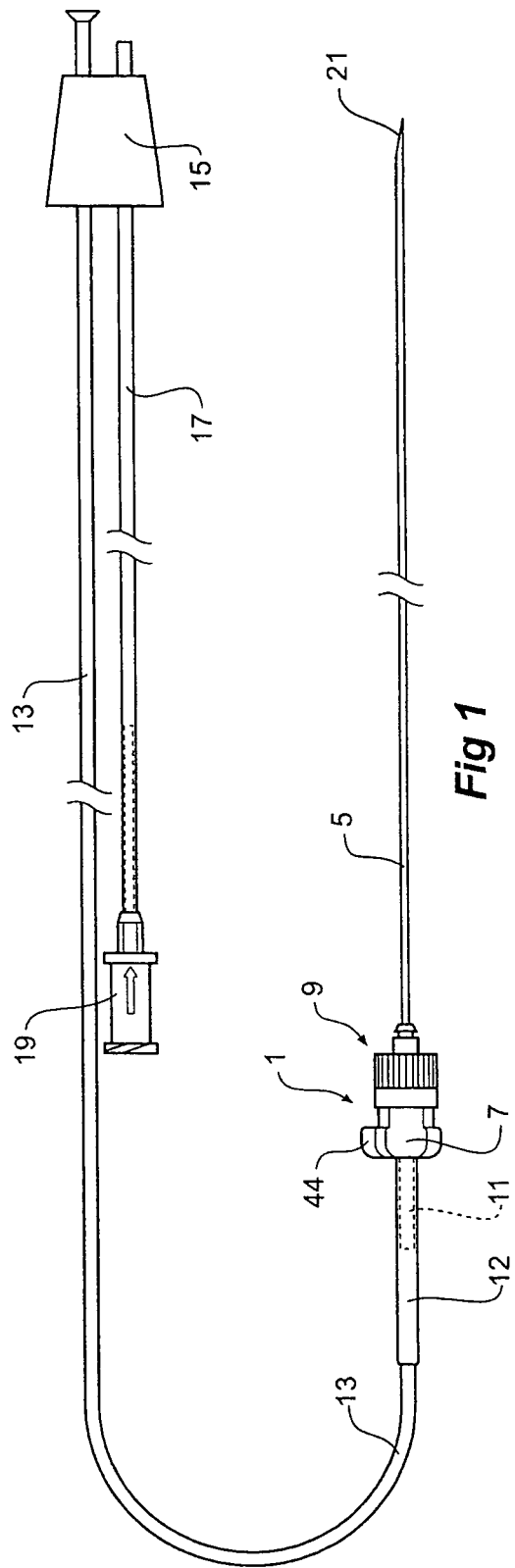
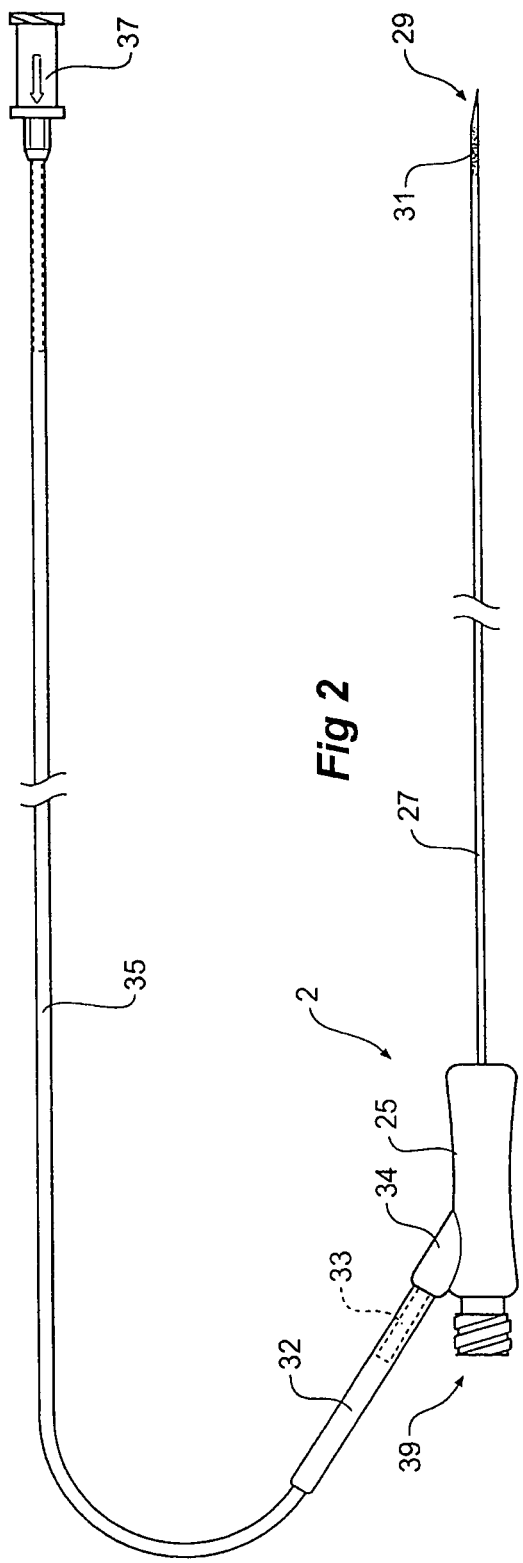
Fig 1
Fig 2

US 7,470,249 B2

ASPIRATION AND FLUSHING NEEDLE

CROSS-REFERENCE TO RELATED APPLICATIONS

This application claims priority of provisional application Ser. No. 60/459,311, filed Apr. 1, 2003.

TECHNICAL FIELD

This invention relates to a medical device and, in particular, to an aspiration and flushing needle arrangement adapted for the removal of oocytes from a female patient.

BACKGROUND OF THE INVENTION

During an oocyte retrieval procedure, a relatively long aspiration cannula may be abdominally inserted into a patient so that the distal end of the cannula is in contact with a patient's ovary. The objective is to puncture an individual follicle on the ovary and withdraw oocytes through the needle. Generally, the proximal end of the cannula is connected to flexible tubing which is, in turn, connected through a test tube to a vacuum source. The vacuum source provides suction via the test tube to the needle to allow aspiration of the oocyte from the follicle. In some medical procedures to retrieve oocytes the physician may puncture several follicles in turn to extract oocytes from each without removal of the aspiration cannula from the patient.

Two different cannula styles are currently used for oocyte retrieval. One style is a single-lumen device. This style requires that any irrigation that is performed to assist with removal of oocytes is conducted through the same fluid path (or lumen) that is used for aspiration. In such instances, if an oocyte is lodged in the fluid path, the oocyte may be actually flushed back into the follicle during the irrigation procedure. Therefore, the use of a single-lumen device may create the potential of losing the oocyte during the irrigation procedure. Accordingly, some physicians prefer the use of a dual-lumen device for oocyte collection procedures. A dual-lumen device has a first fluid path, or lumen, for aspiration and a second fluid path for irrigation. The use of separate paths thereby reduces the possibility of flushing an oocyte out of the aspiration path during an irrigation procedure.

Oocytes are located in a fluid-filled sac or follicle. Before oocytes can be retrieved, a physician needs to be able to accurately puncture each sac prior to retrieval without damaging or losing an oocyte. In order to cleanly puncture the sac, all oocyte collection devices include a cannula having a sharpened bevelled tip. Ideally, the tip is gently inserted into the follicle to puncture the sac and release the oocytes.

It is useful that the physician knows the orientation and location of the tip of the cannula. Therefore, a need exists to provide a means for easily determining the orientation of the bevelled tip and to provide a means for allowing a physician to evenly rotate the tip.

It is an object of this invention to provide a solution to these problems or to at least provide a physician with a useful alternative Throughout this specification the term distal is used to indicate that portion of the apparatus which in use is further away from the physician and the term proximal means the portion of the apparatus which in use is nearer to the physician.

SUMMARY OF THE INVENTION

In one form, therefore, the invention is said to reside in an aspiration and flushing needle assembly having separable flushing and aspiration assemblies, the flushing assembly having a flushing needle connectable to a source of flushing liquid and the aspiration assembly having an aspiration needle connectable to an aspiration arrangement, the flushing and aspiration needle assemblies being connectable for use with the aspiration needle extending coaxially within the flushing needle to the distal end thereof.

In a further form the invention is said to reside in an aspiration and flushing needle assembly including; a handle, an outer needle extending from the handle, a side port in the handle connectable with a source of flushing liquid, an aspiration assembly having a proximal portion connectable to an aspiration assembly and a distally extending cannula, the distally extending cannula extending in use through the handle into the outer needle to the distal end thereof, a connection arrangement on the aspiration cannula to join the aspiration assembly to the handle in use.

In a still further form the invention is said to reside in an aspiration and flushing needle assembly including; a handle, an outer needle extending from the handle, a side port in the handle, the side port being connectable with a source of flushing liquid, a connector portion on the handle, the connector portion being axially aligned with the outer needle, the connector portion having a first connector thereon, an aspiration cannula assembly having an aspiration cannula extending proximally and distally from a grip to define a proximal portion and a distal portion of the aspiration cannula, the proximal portion of the aspiration cannula being connectable to an aspiration assembly, the distal portion of the aspiration cannula in use extending through the handle into a lumen of the outer lumen to the distal end thereof, and a second connector on the grip adapted to connect to the first connector on the connector portion to join the aspiration cannula assembly to the handle for use.

In a still further form the invention is said to reside in an aspiration and flushing needle assembly including; a handle with a handle lumen therein, an outer needle extending from the handle, the outer needle having a needle lumen in fluid communication with the handle lumen, a side port in the handle, the side port having a side port lumen in fluid communication with the handle lumen and being connectable with a source of flushing liquid, a connector portion on the handle, the connector portion having a connector lumen in fluid communication with the handle lumen, the connector portion being axially aligned with the outer needle, the connector portion having a first connector thereon, an aspiration cannula assembly having an aspiration cannula extending proximally and distally from a grip to define a proximal portion and a distal portion of the aspiration cannula, the proximal portion of the aspiration cannula being connectable to an aspiration assembly, the distal portion of the aspiration cannula in use extending into the handle lumen via the connector lumen and to extend into the outer needle lumen to the distal end thereof, and a second connector on the grip adapted to connect to the first on the connector portion to join the aspiration cannula assembly to the handle for use.

It will be noted that in all these embodiments of the invention the aspiration cannula is within the flushing needle. This provides an annular lumen for the flushing media but more importantly it provides an aspiration cannula free of any internal obstructions which enables minimum damage to the oocyte during its travel through the aspiration cannula. The two lumen design provides the ability to aspirate and flush simultaneously. It is preferable to aspirate at a slightly greater flow rate than the rate of supply of flushing liquid to gradually deflate the follicle.

The connector arrangement between the handle and the aspiration cannula may be a press fit, Luer lock type connector, a resilient clip or catch arrangement or any other convenient arrangement.

In a preferred form of the invention the outer needle has a bevelled sharpened tip at its distal end. The bevelled tip may be further sharpened to assist with cutting into a follicle as discussed earlier. The further sharpening may be placed on the inside or the outside of the bevelled sharpened tip.

Preferably the aspiration cannula is adapted to have its distal end terminate just within the bevelled end of the outer needle. Preferably the aspiration cannula is adapted to have its distal end terminate between 0.5 to 1.5 mm from the base of the bevel of the bevelled tip.

Preferably a portion at the distal end of outer needle is treated to improve its ultrasound echo characteristics. Such treatment may include indenting, patterning or knurling or coating with a different material. The treatment to improve the ultrasound echo characteristics may be spaced back from the bevelled tip or may extend partially along the bevelled tip.

There may be provided a tapered extension on the gripper surrounding the aspiration cannula which extends into connector portion in use. There can be provided an O-ring seal on the tapered extension to improve sealing of the aspiration cannula assembly into the handle.

There can be provided alignment detents on the tapered extension which engage with corresponding recesses on connector portion. Tactile indication of the position of the alignment detents may be provided by a protrusion on the grip portion. The position of the corresponding recess on the connector portion is preferably indicated in a tactile manner by it aligned with the side port on the handle. When the side port on the handle is aligned with the protrusion of the grip portion then the alignment detents on the tapered extension will engage with corresponding recesses.

The alignment detents on the tapered extension and the recess on the connector portion may be set so that when fully engaged there is provided a depth setting on the recess in connector portion to ensure distal tip of the aspiration cannula is in a desired position within distal tip of outer needle.

A source of flushing liquid may be connected to side port with a flexible tube.

An aspiration assembly may be connected to proximal end of aspiration cannula with a flexible tube. As discussed earlier the aspiration assembly my include a flexible tubing which is connected to a test tube and a vacuum source also connected to the test tube. The vacuum source provides suction via the test tube to the needle to allow aspiration of the oocyte from the follicle.

Preferably the side port on the handle is aligned with the base of the bevel at the distal tip of the outer needle to facilitate tactile alignment of the tip of the needle whereby a physician can determine the position of the tip of the bevel within a patient with respect to a portion of the assembly outside the patient. The side port also provides the physician with a good gripping portion on the handle to assist with rotation of the aspiration and needle assembly as required.

Preferably the connector portion lumen has internally tapered walls to guide the aspiration cannula into the outer needle lumen.

The aspiration and flushing needle assembly may be supplied in a sterile peel open package and may be intended for one use only.

In a further form the invention is said to reside in an aspiration and flushing needle assembly comprising:
a handle with a handle lumen therein,
an outer needle extending from the handle, the outer needle comprising a needle lumen in fluid communication with the handle lumen, a bevelled sharpened tip at its distal end and a portion at the distal end of outer needle being treated to improve its ultrasound echo characteristics,
a side port in the handle, the side port having a side port lumen in fluid communication with the handle lumen and being connectable with a source of flushing liquid,
a connector portion on the handle, the connector portion having a connector lumen in fluid communication with the handle lumen, the connector portion being axially aligned with the outer needle, the connector portion having a male Luer lock connector thereon,
an aspiration cannula assembly having an aspiration cannula extending proximally and distally from a grip to define a proximal portion and a distal portion of the aspiration cannula, the proximal portion of the aspiration cannula being connectable to an aspiration assembly,
the distal portion of the aspiration cannula in use extending into the handle lumen via the connector lumen and to extend into the outer needle lumen to the distal end thereof, and
a female Luer lock connector on the grip adapted to connect to the male Luer lock connector to join the aspiration cannula assembly to the handle for use.

It is advantageous to supply the aspiration assembly according to the present invention in a disassembled state so that a surgeon or physician can be satisfied that all components are clean and ready to use before assembling them for use. Each component can easily be flushed with flushing medium to ensure that there is no air trapped in them before assembly.

It is particularly advantageous to have a dual lumen needle arrangement with the aspiration cannula concentrically within the flushing cannula.

The flushing lumen or fluid path between the aspiration cannula and the flushing cannula has a dual purpose, not only is it used to convey the flushing medium but it may also be used to control and maintain oocyte temperature during retrieval and in so doing minimizing the damage that may be caused to the oocyte due to rapid temperature changes and exposure to temperatures lower than 37 degrees Celsius. The flushing medium may be heated to a temperature equal to or above the ideal transfer temperature for an oocyte (37° X).

Once vacuum has been applied to the aspiration lumen, fluid is simultaneously passed through the flushing lumen by means of a mechanical syringe pump or similar. The rate at which fluid is passed through the flushing lumen is preferably lower than the aspiration rate so allowing for a positive flow rate to be achieved within the follicle to assist with removal of the oocyte.

The temperature of the flushing medium may be adjusted to achieve an oocyte temperature of 37° C. at the collection point regardless of ambient temperature and the length of aspiration or flushing lines used.

This then generally describes the invention but to assist with understanding, reference will now be made to the accompanying drawings which show preferred embodiments of the invention.

BRIEF DESCRIPTION OF THE DRAWING

In the drawings:

FIG. 1 shows an aspiration cannula assembly according to one embodiment of the invention;

FIG. 2 shows a flushing needle assembly according to one embodiment of the invention;

DETAILED DESCRIPTION

Figure 3:
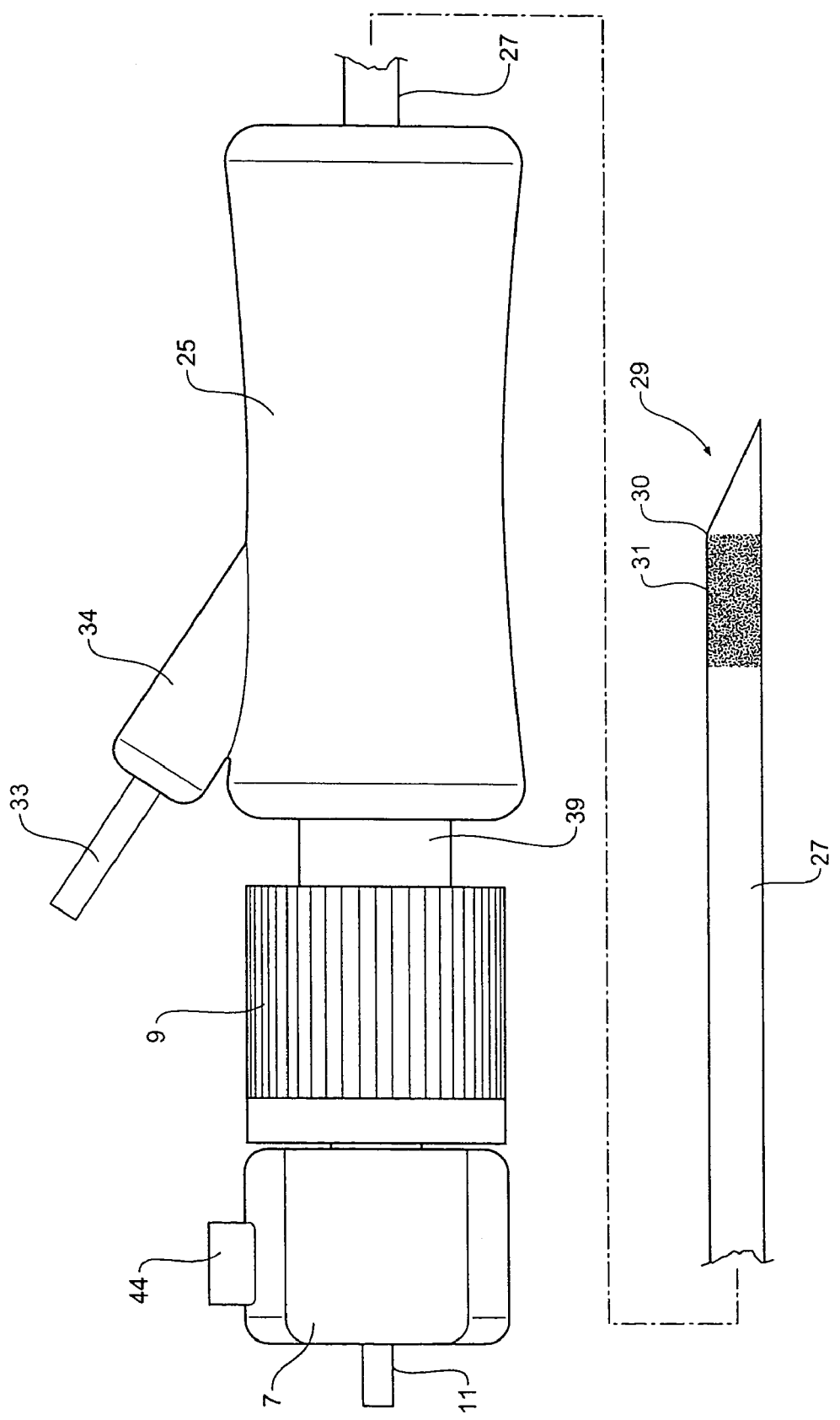
FIG. 3 shows an assembly of the components of FIG. 1 and FIG. 2 in side view.

Now looking more closely at the drawings it will be noted that the aspiration and flushing needle assembly of one embodiment of the present invention comprises an aspiration cannula assembly generally shown as 1 in FIG. 1 and an outer needle assembly generally shown as 2 in FIG. 2.

The aspiration cannula assembly 1 shown in FIG. 1 includes an aspiration cannula 5 extending from a gripper portion 7. A male Luer lock arrangement 9 extends from the gripper portion 7 and is adapted to connect to the flushing needle assembly as will be discussed below. The aspiration cannula 5 extends distally from the gripper portion 7 and also the aspiration cannula 5 extends through the gripper and a portion 11 extends proximally of the gripper portion 7. On to this portion 11 a flexible aspiration line 13 extends to a stopper 15 which can be fitted into a test tube. A heat shrink tubing 12 is fitted over the junction between the portion 11 and the flexible aspiration line 13 to protect the aspiration line 13 at the connection from kinking. Extending through the stopper 15 as well is a vacuum line 17 and a connector 19, the vacuum line allows a source of vacuum to be connected to the aspiration cannula assembly for aspiration.

The flushing needle assembly shown in FIG. 2 comprises a handle 25 with a flushing needle 27 extending distally from the handle 25. Just proximal of the distal tip 29 of the needle 27 is an area of patterning 31 which alters the echo characteristics of the tip of the needle so that with the use of an ultra-sound detector, the tip of the needle may be observed by a physician when it is in use.

Extending from the side of the handle 25 is a side port 33 on an extension 34 of the handle 25 and this side port 33 has extending from it a flushing line 35 which extends to a flushing line connector 37 to which can be connected a source of flushing media. A heat shrink tubing 32 is fitted over the junction between the side port 33 and the flexible flushing line 35 to protect the flushing line 35 at the connection from kinking.

At the proximal end of the handle 25 is a female Luer lock connector 39 to which the male Luer lock connector 9 on the aspiration cannula assembly 1 can be connected as will be explained with respect to FIGS. 3 and 4.

Figure 4:
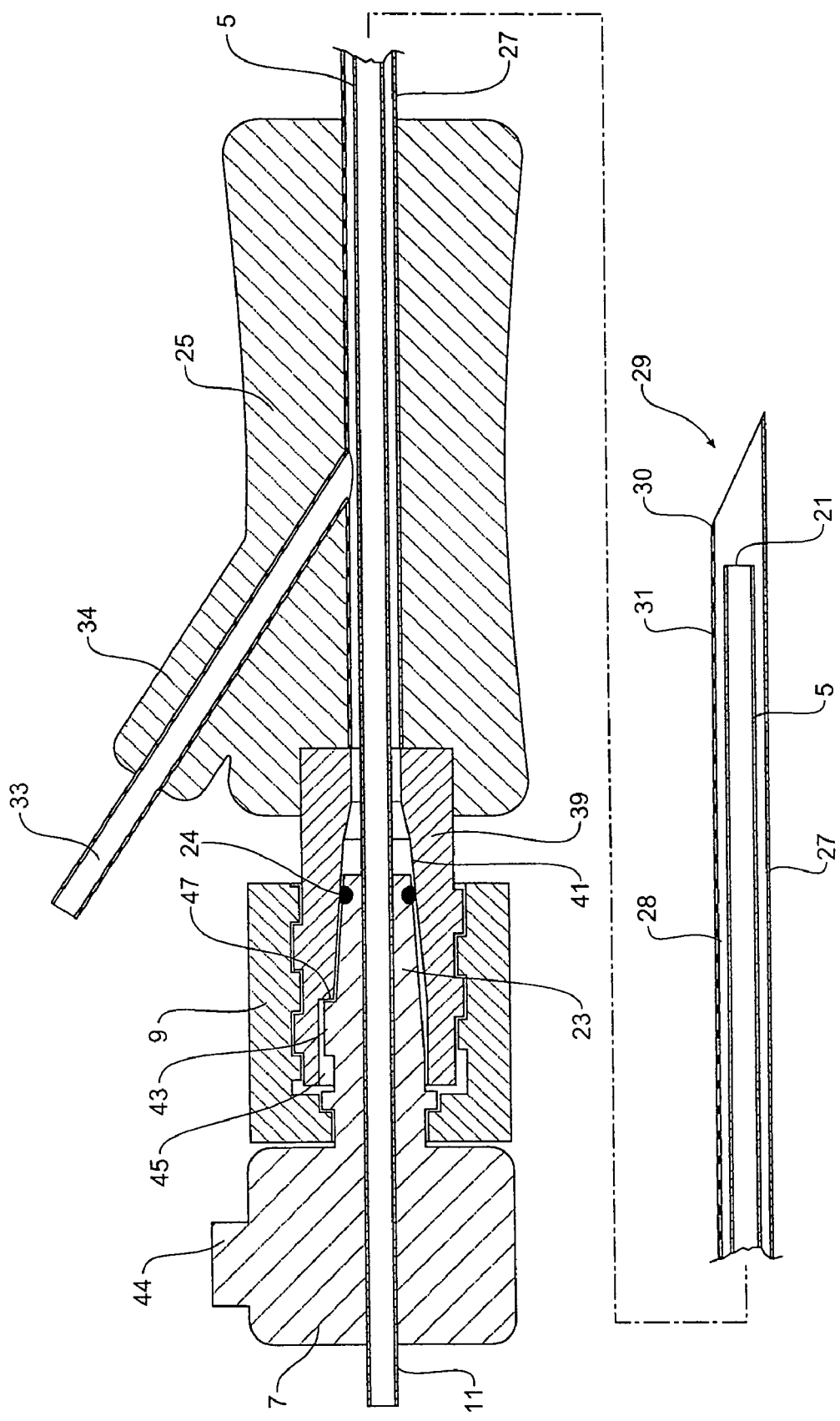
FIG. 4 shows a longitudinal cross section view of the embodiment shown in FIG. 3.

FIGS. 4 and 5 show the connection of the aspiration cannula assembly 1 shown in FIG. 1 to the flushing needle assembly shown in FIG. 2.

To connect the aspiration cannula assembly and the flushing needle assembly the aspiration cannula 5 is inserted in through the connector 39 at the proximal end of the handle 25 so that it fits within the flushing needle 27 and that the distal tip 21 of the aspiration cannula 5 extends to just before the distal tip 29 of the flushing needle 27. Preferably the distal tip 21 of the aspiration cannula 5 terminates between 0.5 to 1.5 millimetres before the base 30 of the bevelled distal tip 29 of the flushing needle 27. At this stage, the male Luer lock connector 9 is engaged with the female Luer lock connector 37 and the two components are joined together.

Now looking at the cross sectional view shown in FIG. 4, it can be seen that the gripper portion 7 includes a distally extending tapered portion 23 with an 'O' ring 24 around it. This distally extending tapered portion 23 extends into a tapered recess 41 in the connector 39 and when fully connected, the 'O' ring 24 seals against the surface 41 to provide a good seal at the proximal end of the handle 25.

To ensure that the two components of the assembly are correctly positioned and so that the spacing between the distal tip 21 of the flushing cannula and the base 30 of the bevel at the tip 29 of the flushing needle is correct, a protrusion 43 on the tapered extension 23 engages into a recess 45 in the wall 41 of the connector 39 until it engages a stop 47 in the recess 45. To assist with alignment of the protrusion 43 and recess 45 there is provided a protrusion 44 on the gripper portion 7.

It will be noted that the tube 35 through the side port 33 of the handle 25 extends into and is in fluid connection with the internal lumen of the flushing needle 27 so that in use flushing liquid is applied into the annular lumen 28 between the flushing needle 27 and the aspiration cannula 5.

Figure 5A:
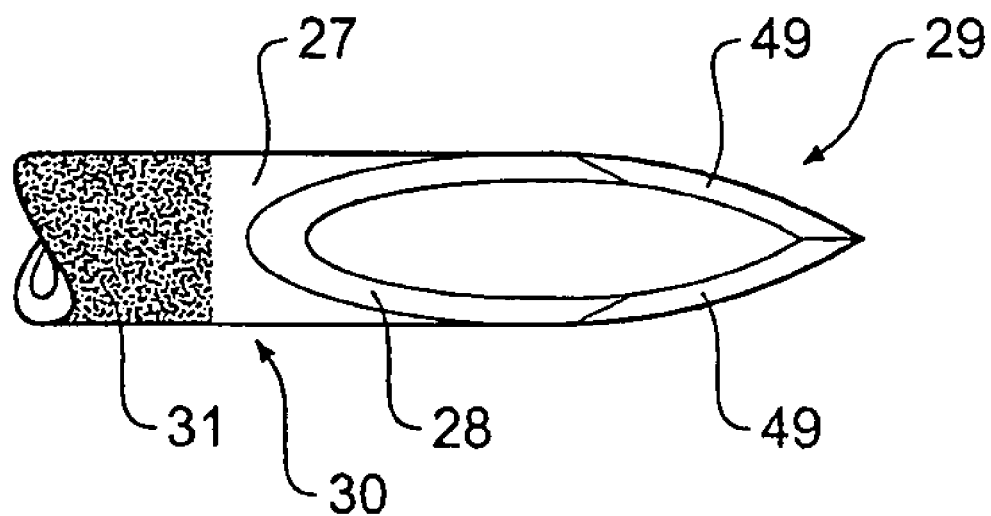
FIG. 5A shows detail of the distal end of the outer needle in one embodiment of the invention.

FIG. 5A shows detail of the distal end of the outer needle in one embodiment of the invention. As can be seen in FIG. 5A the distal tip 29 of the flushing needle 27 has a principal bevel 28 and is further sharpened as shown at 49 with a secondary bevel to enhance the cutting ability of the tip of the flushing needle into a follicle. In this arrangement of sharpening a pair of secondary bevels 49 are placed on the same side of the needle 27 as the bevel 28. It will be noted, too, in FIG. 5A that the area of patterning 31 to provide an echoic tip for ultrasound observation of the tip of the needle is spaced back from the base 30 of the bevel 28.

Figure 5B:
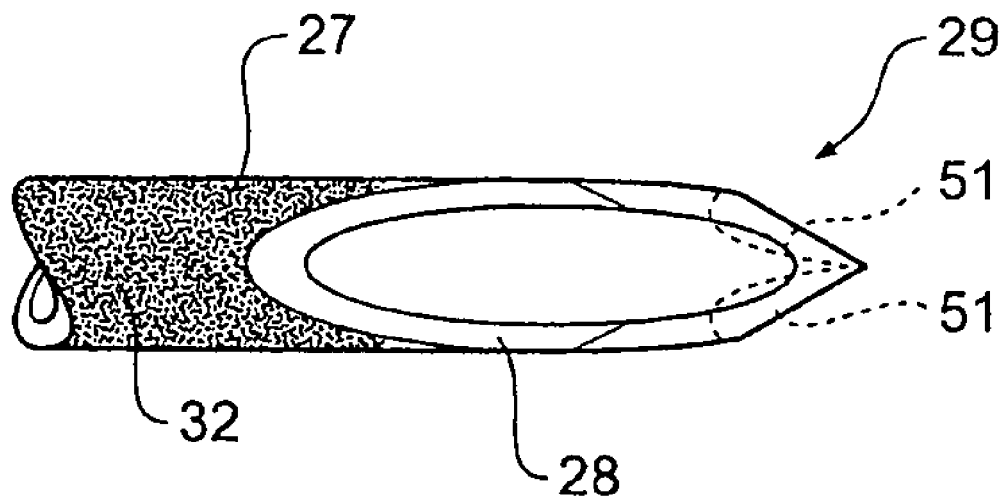
FIG. 5B shows detail of the distal end of the outer needle in an alternative embodiment of the invention.

FIG. 5B shows detail of the distal end of the outer needle in an alternative embodiment of the invention. As can be seen in FIG. 5B the distal tip 29 of the flushing needle 27 has a principal bevel 28 and is further sharpened as shown at 51 with secondary bevels to enhance the cutting ability of the tip of the flushing needle into a follicle. In this arrangement of sharpening a pair of secondary bevels 51 are placed on the opposite side of the needle 27 to the bevel 28. It will be noted, too, in FIG. 5B that the area of patterning 32 to provide an echoic tip for ultrasound observation of the tip of the needle extends past the base 30 of the principal bevel 28 and partially along the bevelled 29.

Throughout this specification various indications have been given as to the scope of the invention, but the invention is not limited to any one of these but may reside in two or more of these combined together. Examples are given for illustrations only and not for limitation.

What is claimed is:

1. An oocyte retrieval aspiration and flushing needle assembly comprising;
   a handle and outer needle assembly,
   the handle and outer needle assembly comprising a handle and an outer needle,
   the handle comprising a handle lumen therein,
   the outer needle extending from the handle, the outer needle having a needle lumen in fluid communication with the handle lumen;
   the outer needle comprising a bevelled sharpened tip at its distal end, a side port in the handle, the side port having a side port lumen in fluid communication with the handle lumen and being connectable with a source of flushing liquid, a connector portion on the handle, the connector portion having a connector lumen in fluid communication with the handle lumen, the connector portion being axially aligned with the outer needle, the connector portion having a first connector thereon, an oocyte aspiration cannula assembly having an oocyte aspiration cannula extending proximally and distally from a grip to define a proximal portion and a distal portion of the aspiration cannula, the proximal portion of the aspiration cannula being connectable to an aspiration assembly, the distal portion of the aspiration cannula in use extending into the handle lumen via the connector lumen and to extend into the outer needle lumen to the distal end thereof, and a second connector on the grip adapted to connect to the first connector on the connector portion to join the aspiration cannula assembly to the handle for use, wherein when assembled the distal end of the aspiration cannula terminates just within the bevelled sharpened tip of the outer needle and the needle lumen extends between aspiration cannula and the outer needle whereby flushing fluid can be supplied through the needle lumen and further including a tapered extension on the grip surrounding the cannula which extends into connector portion in use and alignment detents on the tapered extension which engage with corresponding recesses on the connector portion wherein the alignment detents on the tapered extension and the recess on the connector portion provide a depth setting on the recess in the connector portion to ensure the distal tip of the aspiration cannula is in a desired position within the distal tip of the outer needle.

2. An oocyte retrieval aspiration and flushing needle assembly as in claim 1 wherein the first and second connectors are selected from the group consisting of Luer lock type connectors, push fit connectors, a resilient clip or catch arrangement or any other convenient arrangement.

3. An oocyte retrieval aspiration and flushing needle assembly as in claim 1 wherein the bevelled tip is further sharpened with a secondary bevel to assist with cutting into a follicle.

4. An oocyte retrieval aspiration and flushing needle assembly as in claim 1 wherein the distal end terminates between 0.5 to 1.5 mm proximally from the base of the bevel of the sharpened tip.

5. An oocyte retrieval aspiration and flushing needle assembly as in claim 1 wherein a portion at the distal end of outer needle is treated to improve its ultrasound echo characteristics wherein the treatment is selected from the group consisting of indenting, patterning or knurling or coating with a different material and the treatment is spaced back from the bevelled tip or extends partially along the bevelled tip portion.

6. An oocyte retrieval aspiration and flushing needle assembly as in claim 1 wherein the tapered extension has an O-ring seal on it to improve sealing of the aspiration cannula assembly into the handle.

7. An occyte retrieval aspiration and flushing needle assembly as in claim 1 wherein the connector portion lumen has internally tapered walls to guide the aspiration cannula into the outer needle lumen.

8. An oocyte retrieval aspiration and flushing needle assembly as in claim 1 wherein the aspiration and flushing needle assembly is supplied in a sterile peel open package and is intended for one use only.

9. An oocyte retrieval aspiration and flushing needle assembly as in claim 1 wherein the aspiration and flushing needle assembly is supplied in a disassembled state and intended to be assembled by a physician in use.

10. An oocyte retrieval aspiration and flushing needle assembly comprising;

a handle with a handle lumen therein, an outer needle extending from the handle, the outer needle comprising a needle lumen in fluid communication with the handle lumen, a bevelled sharpened tip at its distal end and a portion at the distal end of outer needle being treated to improve its ultrasound echo characteristics, a side port in the handle, the side port having a side port lumen in fluid communication with the handle lumen and being connectable with a source of flushing liquid, a connector portion on the handle, the connector portion having a connector lumen in fluid communication with the handle lumen, the connector portion being axially aligned with the outer needle, the connector portion having a male Luer lock connector thereon, an oocyte aspiration cannula assembly having an oocyte aspiration cannula extending proximally and distally from a grip to define a proximal portion and a distal portion of the aspiration cannula, the proximal portion of the aspiration cannula being connectable to an aspiration assembly, the distal portion of the aspiration cannula in use extending into the handle lumen via the connector lumen and to extend into the outer needle lumen to the distal end thereof, and a female Luer lock connector on the grip adapted to connect to the male Luer lock connector to join the aspiration cannula assembly to the handle for use and including a tapered extension on the grip surrounding the cannula which extends into connector portion in use and alignment detents on the tapered extension which engage with corresponding recesses on the connector portion wherein the alignment detents on the tapered extension and the recess on the connector portion provide a depth setting on the recess in the connector portion to ensure the distal tip of the aspiration cannula is in a desired position within the distal tip of the outer needle.

* * * * *